(12) United States Patent
Yang et al.

(10) Patent No.: US 7,681,459 B1
(45) Date of Patent: Mar. 23, 2010

(54) MULTI-SCALE & THREE-AXIS SENSING TENSILE TESTING APPARATUS

(75) Inventors: Dehua Yang, Savage, MN (US); Thomas J. Wyrobek, Edina, MN (US)

(73) Assignee: Hysitron, Incorporated, Minneapolis, MN (US)

( * ) Notice: Subject to any disclaimer, the term of this patent is extended or adjusted under 35 U.S.C. 154(b) by 685 days.

(21) Appl. No.: 11/539,028

(22) Filed: Oct. 5, 2006

Related U.S. Application Data

(60) Provisional application No. 60/791,350, filed on Apr. 12, 2006.

(51) Int. Cl.
*G01N 3/32* (2006.01)

(52) U.S. Cl. .......................... 73/856; 73/760

(58) Field of Classification Search ............ 73/760–860
See application file for complete search history.

(56) References Cited

U.S. PATENT DOCUMENTS

| | | | |
|---|---|---|---|
| 2,377,869 A | | 6/1945 | Elliott |
| 3,270,556 A | * | 9/1966 | Henriksen ..................... 73/806 |
| 3,786,676 A | * | 1/1974 | Korolyshun et al. .......... 73/817 |
| 4,297,884 A | | 11/1981 | Leveque et al. |
| 4,848,141 A | | 7/1989 | Oliver et al. |
| 4,856,326 A | * | 8/1989 | Tsukamoto ............... 73/150 A |
| 5,269,190 A | * | 12/1993 | Kramer et al. ................ 73/822 |
| 5,287,749 A | | 2/1994 | Nakamura |
| 5,431,060 A | * | 7/1995 | Lauren ......................... 73/831 |
| 5,452,614 A | | 9/1995 | Kato et al. |
| 5,553,486 A | | 9/1996 | Bonin |
| 5,606,168 A | * | 2/1997 | Chiron et al. ............. 250/443.1 |
| 6,205,862 B1 | | 3/2001 | Nakamura et al. |
| 6,332,364 B1 | * | 12/2001 | Buschmann et al. .......... 73/788 |
| 6,497,921 B1 | * | 12/2002 | Carbonell et al. ........ 427/430.1 |
| 6,892,597 B2 | * | 5/2005 | Tews ...................... 74/471 XY |

(Continued)

FOREIGN PATENT DOCUMENTS

EP  0921388 A2  6/1999

(Continued)

OTHER PUBLICATIONS

D.T. Read et al., Morphology, microstructure, and medical properties of a copper electrodeposit, Microelectronic Engineering 75 (2004) 63-70.

(Continued)

*Primary Examiner*—Max Noori
(74) *Attorney, Agent, or Firm*—Nawrocki, Rooney & Sivertson, P.A.

(57) ABSTRACT

A tensile testing apparatus is provided, and generally includes an X-Y automated stage, and a first specimen holder for holding and transferring force to a specimen to a first portion of a specimen. The first specimen holder is operatively supported by the X-Y automated stage. A Z-automated stage, a multi-function nanotensile transducer head assembly, and a second specimen holder for holding and transferring force to a second portion of the specimen is further provided. The second specimen holder is operatively linked to the Z-automated stage via the nanotensile transducer head assembly. Variable displacement modalities, and non-Z alignment assessment and adjustment are enabled by the multi-function nanotensile transducer head assembly, as well as the X, Y, and Z automated stages.

15 Claims, 1 Drawing Sheet

U.S. PATENT DOCUMENTS 6,983,658 B2 1/2006 Wenski
2001/0013574 A1 9/2001 Warren et al.

FOREIGN PATENT DOCUMENTS

| | | |
|---|---|---|
| JP | 6-123696 | 5/1994 |
| JP | 5-5684 | 1/1996 |
| JP | 9-323570 | 8/1998 |
| JP | 11-218483 | 8/1999 |

OTHER PUBLICATIONS

David T. Read et al., Tensile properties of free-standing aluminum thin films, Scripta Materialia 45 (2001) 583-589.

J.J. Martin, Tension Testing Machines and Extensometers, Metals Handbook, Ninth Ed., vol. 8, Mechanical Testing, American Society for Metals (1985).

Stephan A. Joyce and J.E. Houston, A new force sensor incorporating force-feedback control for interfacial force microscopy; Review of the Scientific Instruments, vol. 62, Issue 3, pp. 710-715 (Mar. 1991).

Ross. C. Thomas, J.E. Houston, Richard M. Crooks, Taisun Kim, Terry A Michalske, Probing Adhesion Forces at the Molecular Scale, J. Amer. Chem. Soc. 117(1995):3830-3834.

Warren, O.L.; Graham, J.F.; Norton, P.R., Tapping mode imaging with an interfacial force microscope, Review of Scientific Instruments, vol. 68, Issue 11, Nov. 1997, pp. 4124-4131.

O.L.Warren, J.F. Graham, and P.R. Norton, Interfacial force microscopy: a novel scanning probe technique for imaging and quantitative measurement of interfacial forces and nanomechanical properties, Phys. Can. 54, 122-136 (1998).

* cited by examiner

MULTI-SCALE & THREE-AXIS SENSING TENSILE TESTING APPARATUS

This is a regular application filed under 35 U.S.C. §111(a) claiming priority under 35 U.S.C. §119(e)(1) of U.S. Prov. Appl. Ser. No. 60/791,350 filed Apr. 12, 2006 and incorporated herein by reference in its entirety.

TECHNICAL FIELD

The present invention generally relates to mechanical test systems, more particularly, to systems, instruments, and/or devices for the application of force to test specimens in furtherance of dynamic testing of same, more particularly still, to a small specimen tensile instrument platform.

BACKGROUND OF THE INVENTION

A tensile test is arguably the most useful single mechanical test that can be performed to evaluate the utility of an engineering or engineered material. Both elastic modulus and yield strength are measured by performing a tensile test.

Small scale material applications, i.e., those implicating materials having a dimensional tolerance within the range of about $10^{-2}$ to $10^{-9}$ meters, are proliferating, with nanoscience and nanotechnology being a well known area of particular focus, and discovery. Nanotechnology, or, as it is sometimes called, molecular manufacturing, is a branch of engineering that deals with the design and manufacture of extremely small devices built at the molecular level of matter. The Institute of Nanotechnology in the U.K. expresses it as "science and technology where dimensions and tolerances in the range of 0.1 nanometer (nm) to 100 nm play a critical role."

As there is no clear correlation between macroscopic and microscopic material properties, the ability to assess the mechanical properties of nano-scale devices or materials would no doubt reveal at least subtle properties of materials previous thought to be well defined. Initial design and prototype phases of nanotechnological product development are direct beneficiaries of instruments and/or systems for assessing mechanical properties of micro/nano materials.

Unlike other mechanical test regimes, tensile tests have the advantage of uniform stress and strain fields, which is why they are used to determine mechanical properties at larger scales. However, conventional tensile tests have disadvantages at smaller scales in that smaller forces are required, and specimen gripping, which is a function of specimen type and geometry, is often difficult.

A variety of challenges are manifest in the testing of small specimen, i.e., those in the millimeter to sub-millimeter range, especially alignment of such specimens with a tensile axis. Peer-reviewed tensile test literature recommends that a given specimen be aligned within a 3-degree range of the tensile axis so as to achieve accurate stress-strain data. As should be readily appreciated, for a specimen of a nominal 1 mm length, a non-Z-axis error of less than 53 µm, or less than 530 µm for a 10 mm specimen is required.

As is well known, there exists a variety of ever increasing small-specimen tensile testing applications, for example, and without limitation: single and multi-component nanocomposite fibers, textiles and plastics; biomedical materials (e.g., sutures, guidewires, signal wires, prosthetic and implantable material); biological materials (e.g., blood vessels, muscles, tendons, organ tissue, skin, etc.); and, biomimetic investigations (e.g., spider silk). Furthermore, and likewise, small-scale pull applications abound, and include, without limitation, stiction, adhesion, deflection and deformation of thin film systems comprising micro-electro-mechanical systems (MEMS); microelectronics interconnection components (e.g., wire conductors, PCB traces, and solder, pad and wire-bond adhesion); and, biomedical coating, component and system interface adhesion assessments. With this backdrop, it remains imperative, among other things, to reduce test related set up time, to improve accuracy and repeatability of small-specimen tensile testing and small-scale pull tests, and to acquire non-tensile axis test data in furtherance of automated specimen assessment and alignment, as well as in connection to additional failure mode assessment.

SUMMARY OF THE INVENTION

The instrument and system of the subject invention is advantageously used to apply and measure forces along a tensile axis (i.e., Z-axis) of a test specimen. The instrument/system enables measurement of material properties at multiple scales, with the range of forces being in the nano-Newton to Newton range. Similarly, displacement and measurement of the specimen are well within the range of nanometers to tens of millimeters.

The instrument of the subject invention generally includes an X-Y automated stage and a first specimen holder for holding a first portion of the specimen and transferring tensile force thereto, the first specimen holder operatively supported by the X-Y automated stage. A Z-automated stage and a multi-function nanotensile transducer head assembly is further provided. Finally, a second specimen holder, for holding a second portion of the specimen and transferring tensile force thereto is provided, the second specimen holder operatively linked to the Z-automated stage via the nanotensile transducer head assembly.

The configuration of a transducer of the multi-function nanotensile transducer head assembly permits select decoupling of a Z displacement sensor, three plate capacitive technology, from the force and motion generator functionality of the assembly so as to enable unrestrained motion and force generation for nanoscale testing of the specimen. Furthermore, via incorporation of additional sensing means, the multi-function nanotensile transducer head assembly permits measurement of forces normal to the tensile axis, i.e., in X and Y directions within a select Z-plane. The subject data acquisition is advantageously made with the specimen mounted in the instrument so as to permit an alignment assessment, i.e., X and Y forces are indicia of misalignment of the tensile axis, i.e., Z-axis, and correction, i.e., via integration of the sensors with X, Y, Z stage motion. Finally, X and Y forces are readily measured as functions of time, with X and Y positions, or Z-displacement providing significant information on failure mechanisms, and associated processes thereof, of the specimen under tensile load.

The subject instrument and system further contemplates microgripping and nano-scale imaging of the specimens under test. Depending upon the testing application, the subject instrument/system may be operated in both open and closed loop scenarios, the latter enabling displacement, strain rate or force-controlled pulling. In addition, dynamic/fatigue testing and automated specimen alignment capabilities are offered. Advantageously, an observation record of the specimen during force and/or motion application is thereby provided. Additional items, advantages and features of the various aspects of the present invention will become apparent from the description of its preferred embodiments, which description should be taken in conjunction with the accompanying drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles, elements and interrelationships there between of the invention.

DETAILED DESCRIPTION OF THE INVENTION

Figure 1:
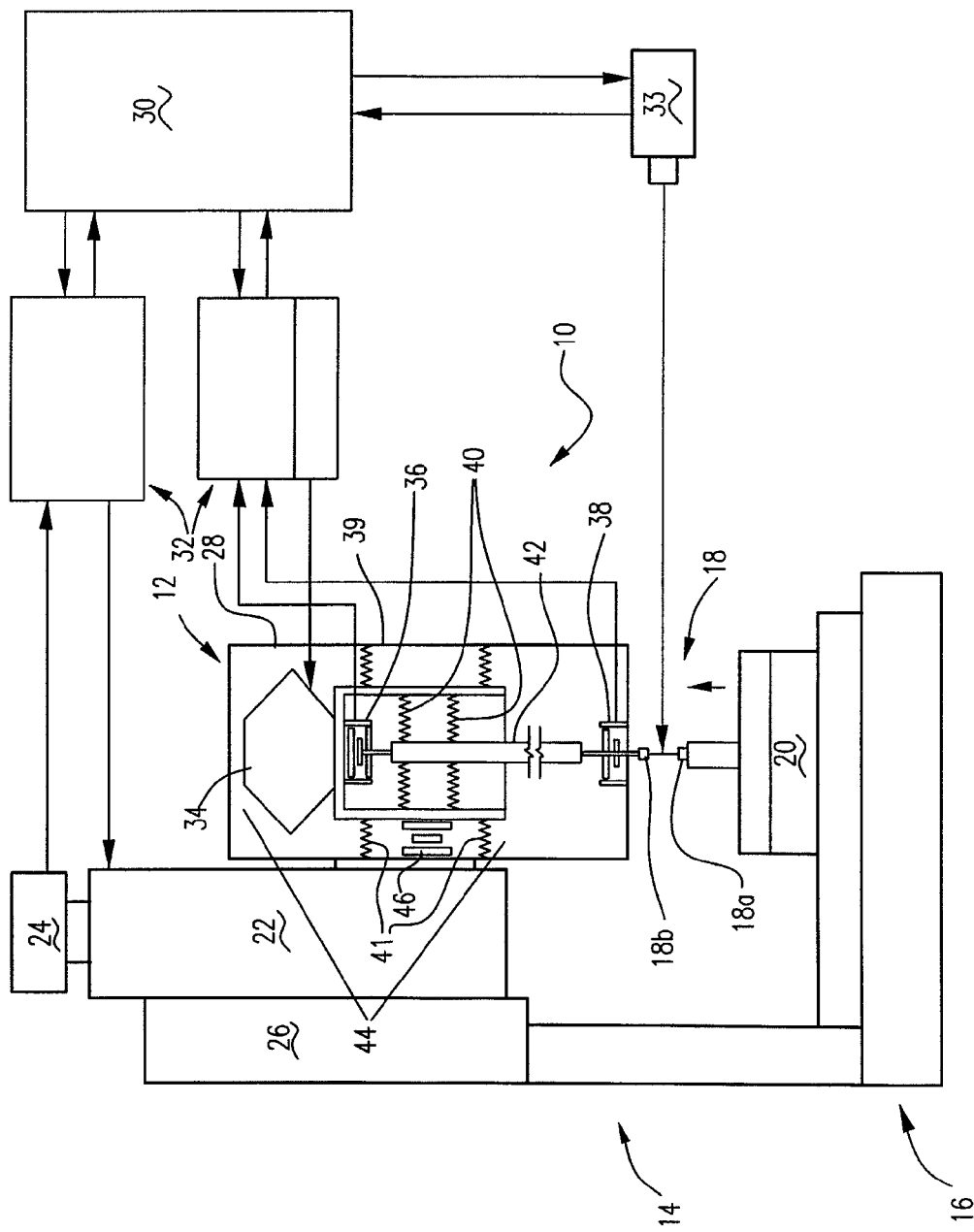
FIG. 1 is a schematic depiction of the tensile testing apparatus of the subject invention, more particularly, a tensile testing system incorporating same.

The contemplated tensile testing instrument/system is characterized by a three part functionality or modality, namely: (1) large displacement; (2) small displacement; and, (3) micro displacement. With reference to FIG. 1, system 10 includes instrument 12 which generally includes a frame 14 having a fixed base or platform 16, and a specimen holder 18, more particularly a lower specimen holder 18a, supported at or by the base 16. The base 16 characteristically and operatively supports X-Y automated stage 20 which is selectively positionable within a plane (i.e., an x-y plane).

The instrument 12 further includes a Z-automated stage 22, with displacement sensor 24, supported by the frame 14, more particularly a vertical arm 26 therefore, for select vertical positioning of a multi-function transducer head assembly 28, over the base 16. Depending or otherwise extending from head assembly 28 is a further specimen holder, more particularly an upper specimen holder 18b.

In connection with the system 10 of FIG. 1, in addition to the aforementioned instrument as described and substantially shown, a personal computer 30 with control and measurement software is likewise provided, and operatively linked to/with one or more controllers 32. Furthermore, an imaging system 33 is contemplated, more particularly, a system comprising optics and charge coupled device (CCD) camera and/or scanning probe microscope (SPM) to facilitate visual inspection and, when operationally linked to personal computer 30, permit storage of the visual record. The subject control mechanism, i.e., the combined hardware and software, enables independent and combined control and measurement in connection with the Z-automated stage, Z-stage displacement sensor, multifunction transducer head assembly components, the X-Y automated specimen stage, and the imaging system. A Windows® based nanotensile graphic user interface (GUI) provides, among other things, load, displacement, and strain rate control routines, automated specimen alignment information, automated X and Y data acquisition and analysis, user defined specimen geometries, surface morphology details and cross-section dimension(s) of the specimen, and, automatic stress-strain and force-displacement data analysis capabilities. As should be readily appreciated, a variety of control mechanisms, as well as modifications to those contemplated, are generally available, and suitable with little or slight alteration based upon instrument functionality and subsequently described.

The transducer head assembly 28 advantageously includes a piezo-actuator 34, first displacement sensor/transducer 36, and second displacement sensor/transducer 38, all of which reside in assembly housing 39. The first displacement sensor 36 is operatively linked to springs 40, rod or shaft 42, and housing 39 so as to delimit a load cell assembly 44, more particularly, precision springs 40 are coupled to the first displacement sensor 36 through shaft 42. The second displacement sensor/transducer 38, as will be later detailed, is operatively disengageable from the load cell assembly.

In connection with the first displacement sensor of the subject instrument, advantageously a Hysitron, Inc., Minneapolis, Minn., standard transducer, see U.S. Pat. No. 5,869,751 (Bonin), incorporated herein by reference, is utilized. While the contemplated transducer includes a capacitive displacement sensor with electrostatic actuation into a three parallel plate system, a reversibly coupleable shaft is further, and more particularly, provided for engaging/disengaging the piezo-actuator and load cell (i.e., the load cell assembly), and the transducer. The shaft, or more generally linkage, is operatively engageable so as to link or couple the piezo-actuator and load cell and second displacement sensor/transducer in the large and small displacement modes, whereas, in the micro displacement mode the shaft is decoupled.

With regard to functionality, large displacement mode operation is characterized by Z-automated stage displacement of the transducer head assembly, more particularly, displacement of the assembly away from the stationary lower specimen holder/base so as to impart a force upon a specimen held between the specimen holders. Commensurate with displacement of the subject head assembly is shaft displacement. The applied force of the Z-automated stage to the specimen is measured through the load cell assembly, with tensile of the specimen measured as the excursion distance of the Z-automated stage/transducer head assembly using methods appropriate for either a stepper, or servo motor. The subject mode is generally, but not necessarily, characterized as having a 10N maximum load, and 150 mm displacement range.

Small displacement mode operation essentially eliminates the Z-automated stage which is selectively set or locked after the appropriate specimen holder spacing is determined with respect to a given specimen. Actuation and measurement exclusively occurs within the head assembly, more particularly, the piezo-actuator pulls the shaft so as to impart a force and displacement on the specimen as the load cell measures force, and the second displacement sensor/transducer, acting again only as a displacement sensor, measures tensile displacement of the specimen. The subject mode generally maintains the 10N maximum load, but scales down the displacement range to 80 μm with a greatly improved resolution of about 0.2 nm.

Finally, the micro displacement mode or operation is utilized to test the smallest of specimens, and exclusively utilizes the second displacement sensor/transducer of the head assembly. The shaft is decoupled from the load cell and piezo-actuator assembly so as to effectively isolate the transducer from the other elements of the nanotensile head assembly. As to specimen testing, the three-plate transducer applies, and measures both the displacement and the force imparted on the specimen during the tensile test using the Hysitron patented technology.

Among several differentiating features of the subject instrument/system is an automated specimen alignment functionality. The subject functionality is achieved via employment of X/Y displacement sensors 46 and a second set of precision springs 41 within the head assembly 28 in a feedback loop to sense any non-Z axis displacement forces, and adjust the X, Y, Z automated stages in such a manner as to eliminate the out-of-axis signals, and effectively aligning the specimen. The alignment assessment, and subsequent adjustments occur without operator intervention. Such feature has particular utility in connection with testing single fibers, see e.g., "Tensile Characteristics and Measurement of Micro/Nano Fiber," Xiao, Tsuchiya & Yang, incorporated herein by reference in its entirety. In addition, the three axis sensing capability can be enabled during the entire tensile test. The display and correlation of the X, Y, Z, displacement provides additional and significant information on failure mechanisms and failure process of the specimen under load. This kind of information may include, for example, crack initiation and propagation, initial failure site location, inhomogeneity of materials, etc.

Furthermore, throughout each of the described modalities, the subject instrument likewise contemplates further capabilities, e.g., application of a time-varying signal on top of the applied load. This dynamic/fatigue tensile testing capability is provided via the head assembly as applied to the piezo-actuator. More complex or advanced tests may be carried out through combination and mixing the testing and operating modes of the subject instrument to maximize the coverage of the specimen size, force or displacement, or to achieve optimal resolutions, e.g., testing a specimen of large size using large displacement mode for most of the test and using small or micro displacement mode to study a portion for detail. A further type of combined test may be run as a combination and mixture of displacement, load or strain rate controlled test, creep, fatigue, stress relation, etc.

Finally, and as previously alluded to, structural and morphological observation of the specimen under test can be examined by incorporation of an optical microscope with a CCD camera or a SPM to further increase dimensional resolution. Such microscopes may be used to provide cross-section dimensional information of the specimen in real time for true stress-strain analysis as well.

There are other variations of this invention which will become obvious to those skilled in the art. It will be understood that this disclosure, in many respects, is only illustrative. Although the various aspects of the present invention have been described with respect to various preferred embodiments thereof, it will be understood that the invention is entitled to protection within the full scope of the appended claims.

What is claimed is:

1. A tensile testing instrument comprising:
   a. an X-Y automated stage;
   b. a first specimen holder for holding a first portion of a specimen, said first specimen holder operatively supported by said X-Y automated stage;
   c. a Z-automated stage;
   d. a multi-function nanotensile transducer head assembly characterized by first and second modalities, said first modality comprising a displacement mode characterized by displacement of said multi-function nanotensile transducer head assembly, said second modality comprising a displacement mode characterized by a fixed position for said multi-function nanotensile transducer head assembly; and,
   e. a second specimen holder for holding a second portion of the specimen, said second specimen holder operatively linked to said Z-automated stage via said nanotensile transducer head assembly.

2. The tensile testing instrument of claim 1 wherein said second modality is further characterized by actuation of a first subassembly of said multi-function nanotensile transducer head assembly so as to impart a force to a specimen through said first specimen holder.

3. The tensile testing instrument of claim 2 wherein a third modality of said multi-function nanotensile transducer head assembly likewise comprises a displacement mode characterized by a fixed position for said multi-function nanotensile transducer head assembly.

4. The tensile testing instrument of claim 3 wherein said third modality is further characterized by actuation of a second subassembly of said multi-function nanotensile transducer head assembly so as to impart a force to a specimen through said first specimen holder.

5. The tensile testing instrument of claim 4 wherein said first and second subassemblies of said multi-function nanotensile transducer head assembly are operatively disengageable.

6. A tensile testing instrument comprising:
   a. an X-Y automated stage;
   b. a first specimen holder for holding a first portion of a specimen, said first specimen holder operatively supported by said X-Y automated stage;
   c. a Z-automated stage;
   d. a multi-function nanotensile transducer head assembly comprising a first displacement sensing means, a piezo-actuator subassembly and a second displacement means; and,
   e. a second specimen holder for holding a second portion of the specimen, said second specimen holder operatively linked to said Z-automated stage via said nanotensile transducer head assembly.

7. The tensile testing instrument of claim 6 wherein said second displacement means is operatively isolatable.

8. The tensile testing instrument of claim 6 wherein a first modality for the instrument is characterized by translation of said multi-function nanotensile transducer head assembly.

9. The tensile testing instrument of claim 8 wherein a second modality for the instrument is characterized by actuation of said piezo-actuator subassembly.

10. The tensile testing instrument of claim 9 wherein a third modality for the instrument is characterized by actuation of said second displacement sensing means.

11. A multi-function test assembly for operative engagement with a specimen holder of a tensile testing apparatus, said multi-function test assembly comprising a piezo-actuator, force sensing means, and displacement sensing means, said force sensing means operatively linked to said piezo-actuator so as to delimit a load cell subassembly, said displacement sensing means being operatively coupled to said load cell subassembly by a shaft and disengageable therefrom, said shaft adapted so as to disengage said displacement sensing means from said load cell subassembly.

12. A multi-function test assembly for operative engagement with a specimen holder of a tensile testing apparatus, said multi-function test assembly comprising a piezo-actuator, force sensing means, and displacement sensing means, said force sensing means operatively linked to said piezo-actuator so as to delimit a load cell subassembly, said displacement sensing means being operatively coupled to said load cell subassembly by a shaft and disengageable therefrom, said load cell subassembly having a first operative status delimited by displacement of said load cell subassembly by said displacement means.

13. The multi-function test assembly of claim 12 wherein said first operative status is further delimited by a decoupling of said displacement sensing means from said load cell subassembly.

14. The multi-function test assembly of claim 12 wherein said load cell subassembly has a second operative status delimited by operative disengagement of said load cell subassembly from said displacement means.

15. The multi-function test assembly of claim 14 wherein said second operative status is further delimited by coupling of said displacement sensing means to said load cell subassembly.

* * * * *